United States Patent [19]

Schuetz et al.

[11] Patent Number: 5,008,438
[45] Date of Patent: Apr. 16, 1991

[54] ORTHO-SUBSTITUTED PHENOL ETHERS AND FUNGICIDES WHICH CONTAIN THESE COMPOUNDS

[75] Inventors: Franz Schuetz, Ludwigshafen; Siegbert Brand, Weinhelm; Bernd Wenderoth, Lampertheim; Hubert Sauter, Mannheim; Eberhard Ammermann, Ludwigshafen; Cisela Lorenz, Neustadt, all of Fed. Rep. of Germany

[73] Assignee: BASF Aktiengesellschaft, Ludwigshafen, Fed. Rep. of Germany

[21] Appl. No.: 322,727

[22] Filed: Mar. 13, 1989

[30] Foreign Application Priority Data

Mar. 31, 1988 [DE] Fed. Rep. of Germany ....... 3811012

[51] Int. Cl.$^5$ ............................................. C07C 69/76
[52] U.S. Cl. .......................................... 560/55; 560/9; 560/39; 560/45
[58] Field of Search .......................... 560/55, 9, 39, 45; 514/532, 538

[56] References Cited

U.S. PATENT DOCUMENTS 4,709,078 11/1987 Schirmer ................................ 560/60
4,723,034 2/1988 Schirmer ................................ 560/60

FOREIGN PATENT DOCUMENTS 0229974 12/1986 European Pat. Off. .
0251082 6/1987 European Pat. Off. .
0253213 7/1987 European Pat. Off. .
0280185 2/1988 European Pat. Off. .
0226917 12/1988 European Pat. Off. .

1164152 9/1964 Fed. Rep. of Germany .
3519282 12/1986 Fed. Rep. of Germany .
3545319 6/1987 Fed. Rep. of Germany .

*Primary Examiner*—Paul J. Killos
*Attorney, Agent, or Firm*—Oblon, Spivak, McClelland, Maier & Neustadt

[57] ABSTRACT

Ortho-substituted phenol ethers of the general formula I

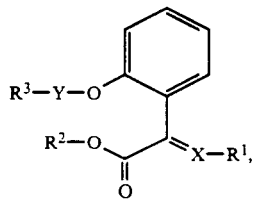

where
$R^1$ is $C_1-C_4$-alkyl, $C_1-C_4$-alkoxy, $C_1-C_4$-alkylthio or amino which is unsubstituted or mono- or disubstituted by $C_1-C_4$-alkyl,
$R^2$ is $C_1-C_4$-alkyl,
$R^3$ is aryloxy, arylthio or arylalkoxy, the aromatic ring being unsubstituted or substituted by one or more of the following radicals: halogen, $C_1-C_6$-alkyl, $C_1-C_6$-alkoxy, $C_1-C_4$-alkylthio, $C_1-C_2$-haloalkyl, aryl, aryl-$C_1-C_2$-alkoxy, $C_1-C_4$-alkylcarbonyl, mono- or di-$C_1-C_4$-alkylsubstituted amino, cyano, nitro,
X is CH or N, and
Y is saturated or unsaturated $C_2-C_{12}$-alkylene,
and fungicides containing these compounds.

7 Claims, No Drawings

ORTHO-SUBSTITUTED PHENOL ETHERS AND FUNGICIDES WHICH CONTAIN THESE COMPOUNDS

The present invention relates to useful novel ortho-substituted phenol ethers having a fungicidal action, and fungicides which contain these compounds.

It is known that methyl acrylates, e.g. methyl α-(2-benzyloxyphenyl)-β-methoxyacrylate (DE-35 19 282.8) or methyl α-(2-phenoxymethylenephenyl)-β-methoxyacrylate (DE-35 45 319.2) can be used as fungicides. However, their fungicidal action is unsatisfactory.

We have found that ortho-substituted phenol ethers of the general formula I

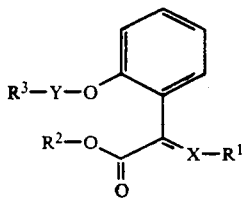

where $R^1$ is $C_1$-$C_4$-alkyl, $C_1$-$C_4$-alkoxy or $C_1$-$C_4$-alkylthio or is amino which is unsubstituted or monosubstituted or disubstituted by $C_1$-$C_4$-alkyl, $R^2$ is $C_1$-$C_4$-alkyl, $R^3$ is aryloxy, arylthio or arylalkoxy, the aromatic ring being unsubstituted or substituted by 1, 2 or 3 of the radicals halogen, $C_1$-$C_6$-alkyl, $C_1$-$C_6$-alkoxy, $C_1$-$C_4$-alkylthio, $C_1$- or $C_2$-haloalkyl, aryl, aryl-$C_1$- or -$C_2$-alkoxy, $C_1$-$C_4$-alkylcarbonyl, mono- or di-$C_1$-$C_4$-alkyl-substituted amino, cyano and nitro, X is CH or N and Y is saturated or unsaturated $C_2$-$C_{12}$-alkylene, have an excellent fungicidal action which is better than that of known methyl acrylates.

The radicals mentioned in the general formula can, for example, have the following meanings: $R^1$ may be, for example, straight-chain or branched $C_1$-$C_4$-alkyl (e.g. methyl, ethyl, n- or isopropyl, n-, iso-, sec-or tert-butyl), $C_1$-$C_4$-alkoxy (e.g. methoxy, ethoxy, n- or isopropoxy, n-, iso-, sec- or tert-butoxy), $C_1$-$C_4$-alkylthio (e.g. methylthio, ethylthio, n- or isopropylthio, n-, iso-, sec- or tert-butylthio) or amino which is unsubstituted or monosubstituted or disubstituted by $C_1$-$C_4$-alkyl (e.g. amino, methylamino, dimethylamino, diethylamino or diisopropyl-amino).

$R^2$ may be, for example, $C_1$-$C_4$-alkyl (e.g. methyl, ethyl, n- or isopropyl, n-, iso-, sec- or tert-butyl).

$R^3$ may be, for example, aryloxy (phenoxy, 1-naphthyloxy or 2-naphthyloxy), arylthio (phenylthio) or arylalkoxy (benzyloxy), and the aromatic ring may be unsubstituted or substituted by 1, 2 or 3 of the following radicals: halogen (e.g. fluorine, chlorine or bromine), $C_1$-$C_6$-alkyl (e.g. methyl, ethyl, n- or isopropyl, n-, iso-, sec- or tert-butyl, n-, iso-, sec-, tert- or neopentyl or hexyl), $C_1$-$C_6$-alkoxy (e.g. methoxy, ethoxy, n- or isopropoxy, n-, iso-, sec- or tert-butoxy), $C_1$-$C_4$-alkylthio (e.g. methylthio or ethylthio), $C_1$- or $C_2$-haloalkyl (e.g. difluoromethyl or trifluoromethyl), aryl (e.g. phenyl), aryl-$C_1$- or -$C_2$-alkoxy (e.g. benzyloxy), $C_1$-$C_4$-alkylcarbonyl (e.g. acetyl), amino which is monosubstituted or disubstituted by $C_1$-$C_4$-alkyl (e.g. dimethylamino), cyano or nitro.

The radical X mentioned in the general formula I may be CH or N, and Y may be, for example, straight-chain $C_2$-$C_{12}$-alkylene (e.g. ethylene, propylene, butylene, pentylene, hexylene, heptylene, octylene, nonylene or decylene), branched $C_2$-$C_{12}$-alkylene (e.g. methylethylene) or $C_4$-$C_{12}$-alkenylene (e.g. butenylene).

The novel compounds can be prepared, for example, by the following processes:

The compounds of the general formula Ia (where $R^1$ is alkoxy, X is CH, $R^2$, $R^3$ and Y have the abovementioned meanings) are prepared, for example, by reacting an ortho-substituted phenylacetate of the general formula III with methyl formate using a base (e.g. sodium hydride) in an inert solvent, e.g. diethyl ether or tetrahydrofuran (cf. Ann. Chem. 424 (1921), 214). The resulting hydroxymethylene derivatives of the general formula IV, which may also occur in equilibrium with the formyl derivatives V, are reacted with an alkylating agent (e.g. dimethyl sulfate) in the presence of a base (e.g. potassium carbonate) in a diluent (e.g. acetone). In the following formulae, Alk is a $C_1$-$C_4$-alkyl group and L is a leaving group (e.g. methylsulfate).

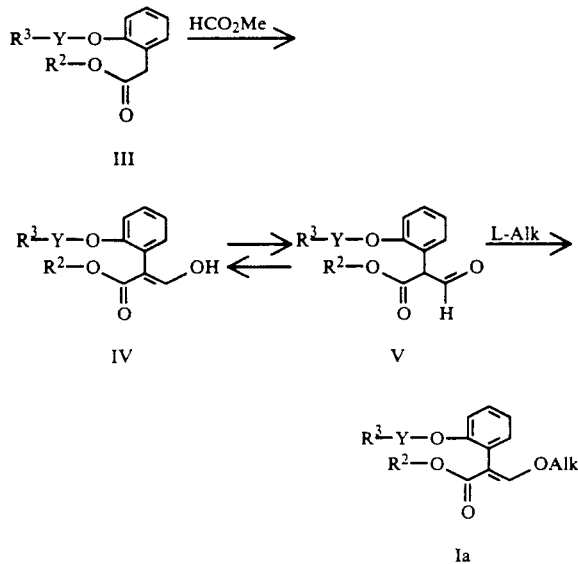

To prepare the compounds of the general formula Ib (where $R^1$ is alkylthio, X is CH and $R^2$, $R^3$ and Y have the abovementioned meanings), the hydroxymethylene derivatives IV, which may also occur in equilibrium with the formyl derivatives V, are first reacted with a sulfonyl chloride, e.g. methanesulfonyl chloride (where R' is methyl), trifluoromethanesulfonyl chloride (where R' is trifluoromethyl) or p-toluenesulfonyl chloride (where R' is p-methylphenyl) in the presence of a base (e.g. triethylamine) to give compounds of the general formula VI. The desired compounds Ib are then obtained by reacting VI with an alkyl thiolate Alk S$^-$, e.g. sodium thiomethylate.

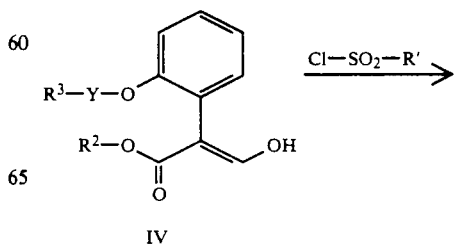

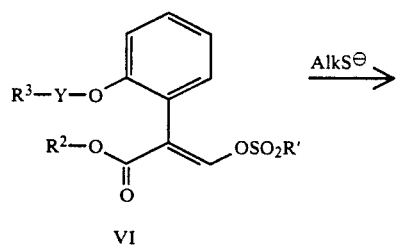

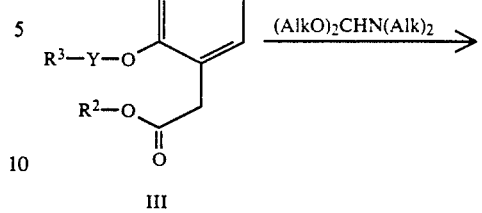

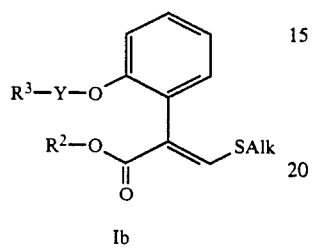

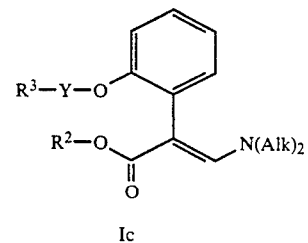

The compounds of the general formula Ic (where $R^1$ is alkylamino or dialkylamino, X is CH and $R^2$, $R^3$ and Y have the abovementioned meanings) are prepared by reacting a hydroxymethylene derivative IV, which may also occur in equilibrium with V, with a primary or secondary amine. Alternatively, it is also possible to react an alkali metal salt of IV with a hydrochloride of a primary or secondary amine, with liberation of sodium chloride (cf. Ann. Chim. [10] 18 (1932), 103).

The novel compounds of the general formula Id (where $R^1$ is alkyl, X is CH and $R^2$, $R^3$ and Y have the abovementioned meanings) can be prepared by subjecting an alpha-ketocarboxylate of the general formula II to a Wittig reaction with an alkyltriphenylphosphonium bromide in the presence of a base (e.g. n-butyllithium, sodium methylate, potassium tert-butylate or sodium hydride) in an inert solvent (e.g. diethyl ether, tetrahydrofuran, dimethylformamide or dimethyl sulfoxide) (cf. Methoden der organischen Chemie, Volume E1, page 710, Thieme, Stuttgart 1982).

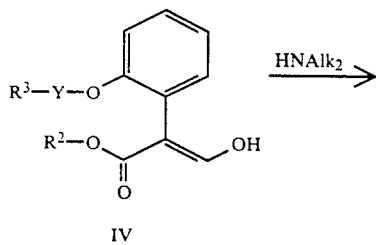

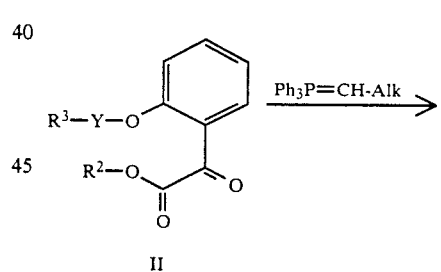

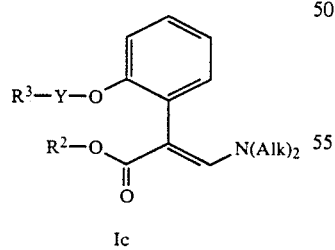

Compounds of the formula Ic are also obtained if an ortho-substituted phenylacetate of the general formula III is reacted with a dialkylformamide dialkyl acetal or with an animal alkyl ester, the reaction being catalyzed, if necessary, by p-toluenesulfonic acid (cf. for example Chem. Ber. 97 (1964), 3396).

The alpha-ketocarboxylates of the general formula II are novel. They can be prepared, for example, by reacting the corresponding aromatic Grignard compound VII with an imidazolide of the formula VIII (J. Org. Chem. 46 (1981), 211). $R^2$, $R^3$ and Y have the abovementioned meanings.

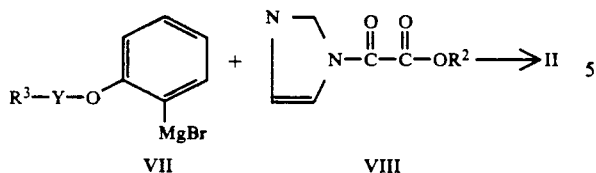

The novel compounds of the general formula Ie (where $R^1$ is alkoxy, X is N and $R^2$, $R^3$ and Y have the abovementioned meanings) are obtained by reacting an alpha-ketocarboxylate II with an O-alkyl-substituted hydroxylamine hydrochloride in the presence of a base (e.g. sodium carbonate or sodium acetate) in an inert solvent (e.g. methanol). The novel compounds Ie are also obtained if the alpha-ketocarboxylate II is first reacted with hydroxylamine and the resulting oxime is then reacted with an alkylating agent of the formula Alk—L (where L is halogen, e.g. Cl, Br or I).

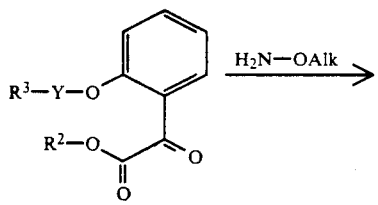

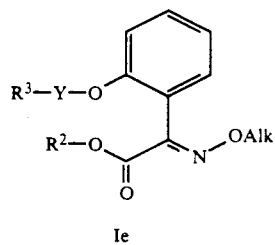

A preparation process for ortho-substituted phenol ethers of the general formula If (where $R^1$ is alkylamino or dialkylamino, X is N and $R^2$, $R^3$ and Y have the abovementioned meanings) is, for example, the following: an alpha-ketocarboxylate of the formula II is reacted with a substituted hydrazine in the presence of a protic acid (e.g. hydrochloric acid) in a suitable solvent (e.g. methanol) (cf. Liebigs Ann. Chem. 722 (1969), 29).

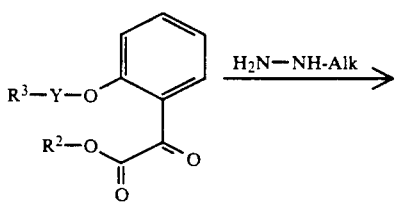

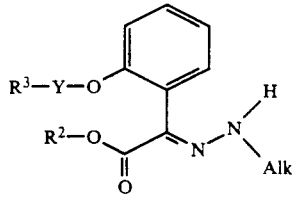

The ortho-substituted phenylacetates III which are required as starting compounds are prepared, for example, by alkylating a methyl ortho-hydroxyphenylacetate

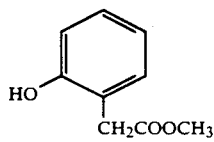

with an omega-aryloxyalkyl halide $R^3$—Y—Halogen by a conventional method (Methoden der organischen Chemie, Volume 6/3, page 54, Thieme, Stuttgart 1965). In the same way, an ortho-hydroxyphenyl bromide

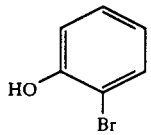

and an omega-aryloxyalkyl halide $R^3$—Y—Halogen give an ortho-substituted phenyl bromide

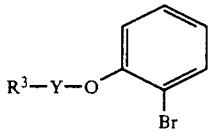

which is further reacted by a standard method to give the Grignard compounds VII required as starting compounds.

Omega-aryloxyalkyl halides $R^3$—Y—Halogen are known compounds or can readily be prepared by known processes, for example by monoalkylation of phenols with aliphatic dihaloalkanes (e.g. 1,2-dibromoethane, 1,3-dibromopropane, 1,4-dibromobutane, 1,5-dibromopropane, 1,6-dibromohexane or 1,7-dibromoheptane).

Because of the C═C or C═N double bond, some of the novel compounds of the formula I are obtained in the preparation in the form of E/Z isomer mixtures. These can be separated into the individual components in a conventional manner, for example by crystallization or chromatography. The invention embraces both the individual isomeric compounds and their mixtures.

The Example which follows illustrates the preparation of the novel active ingredients.

METHOD 1

Methyl 2-(4-phenoxybut-1-yloxy)-phenylacetate 28.2 g (0.17 mole) of methyl 2-hydroxyphenylacetate, 25.8 g (0.19 mole) of potassium carbonate and 38.9 g (0.17 mole) of 4-phenoxybutyl bromide in 400 ml of dimethylformamide are stirred for 24 hours at 70° C. Thereafter, the solvent is stripped off and the residue is taken up in diethyl ether. The solution is extracted several times with water and saturated sodium carbonate solution and the organic phase is dried over MgSO4. The oil obtained after removal of the solvent is purified by chromatography over silica gel (cyclohexane/ethyl acetate). Yield: 31 g (58%).

METHOD 2

Methyl alpha-[2-(4-phenoxybut-1-yloxy)-phenyl]-β-hydroxyacrylate

A mixture of 30 g (0.10 mole) of methyl 2-(4-phenoxybut-1-yloxy)-phenylacetate, 12.5 g (0.21 mole) of methyl formate and 100 ml of diethyl ether is added dropwise at room temperature to a suspension of 3.4 g (0.14 mole) of sodium hydride in 50 ml of diethyl ether. The mixture is stirred for 12 hours at room temperature and is then hydrolyzed by adding ice. The aqueous, alkaline phase is extracted with diethyl ether, acidified with dilute HCl and again extracted by shaking with diethyl ether. After the organic phase has been evaporated down, 21 g (71%) of methyl alpha-[2-(4-phenoxybut-1-yloxy)-phenyl]-β-hydroxyacrylate are obtained.

EXAMPLE 1

Methyl alpha-[2-(4-phenoxybut-1-phenyl]-β-methoxyacrylate 20 g (0.06 mole) of the compound obtained above are stirred together with 7.4 g (0.06 mole) of dimethyl sulfate and 8.0 g (0.06 mole) of potassium carbonate in 150 ml of acetone for 48 hours at room temperature. Thereafter, the precipitate is filtered off, the acetone is stripped off and the residue is taken up in diethyl ether. The organic phase is washed with semiconcentrated ammonia and water, dried and evaporated down. 15.2 g (73%) of the title compound are obtained as a pure E isomer in the form of colorless crystals of melting point 88° C. (compound No. 97).

The compounds below can be prepared in a similar manner:

TABLE 1

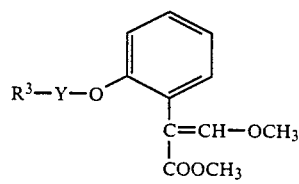

Compounds of the formula I
($R^1$ = $OCH_3$, $R^2$ = $CH_3$, X = CH)
The configuration statement relates to the β-methoxyacrylate group

| No. | $R^3$ | Y | mp. (isomer) |
|---|---|---|---|
| 1 | $C_6H_5$—O— (= phenoxy) | —$CH_2$—$CH_2$— | |
| 2 | 2-F—$C_6H_4$—O— | —$CH_2$—$CH_2$— | |
| 3 | 3-F—$C_6H_4$—O— | —$CH_2$—$CH_2$— | |
| 4 | 4-F—$C_6H_4$—O— | —$CH_2$—$CH_2$— | |
| 5 | 2-Cl—$C_6H_4$—O— | —$CH_2$—$CH_2$— | |
| 6 | 3-Cl—$C_6H_4$—O— | —$CH_2$—$CH_2$— | |
| 7 | 4-Cl—$C_6H_4$—O— | —$CH_2$—$CH_2$— | |
| 8 | 2-$CH_3$—$C_6H_4$—O— | —$CH_2$—$CH_2$— | |
| 9 | 3-$CH_3$—$C_6H_4$—O— | —$CH_2$—$CH_2$— | |
| 10 | 4-$CH_3$—$C_6H_4$—O— | —$CH_2$—$CH_2$— | |
| 11 | 2-$OCH_3$—$C_6H_4$—O— | —$CH_2$—$CH_2$— | |
| 12 | 3-$OCH_3$—$C_6H_4$—O— | —$CH_2$—$CH_2$— | |
| 13 | 4-$OCH_3$—$C_6H_4$—O— | —$CH_2$—$CH_2$— | |
| 14 | 4-t-$C_4H_9$—$C_6H_4$—O— | —$CH_2$—$CH_2$— | |
| 15 | 4-$OC_2H_5$—$C_6H_4$—O— | —$CH_2$—$CH_2$— | |
| 16 | 4-$CF_3$—$C_6H_4$—O— | —$CH_2$—$CH_2$— | |
| 17 | 4-$C_6H_5$—$C_6H_4$—O— | —$CH_2$—$CH_2$— | |
| 18 | 4-($C_6H_5$—$CH_2$—O—)—$C_6H_4$—O— | —$CH_2$—$CH_2$— | |
| 19 | 2,4,6-$Cl_3$—$C_6H_2$—O— | —$CH_2$—$CH_2$— | |
| 20 | 2,4,6-$(CH_3)_3$—$C_6H_2$—O— | —$CH_2$—$CH_2$ | |
| 21 | 1-naphthol | —$CH_2$—$CH_2$— | |
| 22 | 2-naphthol | —$CH_2$—$CH_2$— | |
| 23 | 2-Br—$C_6H_4$—O— | —$CH_2$—$CH_2$— | |
| 24 | 3-Br—$C_6H_4$—O— | —$CH_2$—$CH_2$— | |
| 25 | 4-Br—$C_6H_4$—O— | —$CH_2$—$CH_2$— | |
| 26 | 2-$CF_3$—$C_6H_4$—O— | —$CH_2$—$CH_2$— | |
| 27 | 3-$CF_3$—$C_6H_4$—O— | —$CH_2$—$CH_2$— | |
| 28 | 4-CN—$C_6H_4$—O— | —$CH_2$—$CH_2$— | |
| 29 | 4-$CH_3CO$—$C_6H_4$—O— | —$CH_2$—$CH_2$— | |
| 30 | 3-$(CH_3)_2N$—$C_6H_4$—O— | —$CH_2$—$CH_2$— | |
| 31 | 4-$SCH_3$—$C_6H_4$—O— | —$CH_2$—$CH_2$— | |
| 32 | 2-$OC_2H_5$—$C_6H_4$—O— | —$CH_2$—$CH_2$— | |
| 33 | 4-t-butoxy-$C_6H_4$—O— | —$CH_2$—$CH_2$— | |
| 34 | 2,4-$Cl_2$—$C_6H_3$—O— | —$CH_2$—$CH_2$— | |
| 35 | 3,4-$Cl_2$—$C_6H_3$—O— | —$CH_2$—$CH_2$— | |
| 36 | 2,5-$Cl_2$—$C_6H_3$—O— | —$CH_2$—$CH_2$— | |

TABLE 1-continued $$R^3-Y-O-C_6H_4-C(COOCH_3)=CH-OCH_3$$

Compounds of the formula I
($R^1$ = OCH$_3$, $R^2$ = CH$_3$, X = CH)
The configuration statement relates to the β-methoxyacrylate group

| No. | $R^3$ | Y | mp. (isomer) |
|---|---|---|---|
| 37 | 2,6-Cl$_2$—C$_6$H$_3$—O— | —CH$_2$—CH$_2$— | |
| 38 | 2,4,5-Cl$_3$—C$_6$H$_2$—O— | —CH$_2$—CH$_2$— | |
| 39 | 2-Cl-4-F—C$_6$H$_3$—O— | —CH$_2$—CH$_2$— | |
| 40 | 2-Cl-4-Br—C$_6$H$_3$—O— | —CH$_2$—CH$_2$— | |
| 41 | 2,4-(CH$_3$)$_2$—C$_6$H$_3$—O— | —CH$_2$—CH$_2$— | |
| 42 | 2-CH$_3$-4-t-C$_4$H$_9$—C$_6$H$_3$—O— | —CH$_2$—CH$_2$— | |
| 43 | 2-CH$_3$-4-Cl—C$_6$H$_3$—O— | —CH$_2$—CH$_2$— | |
| 44 | 2-CH$_3$-4,6-Cl$_2$—C$_6$H$_2$—O— | —CH$_2$—CH$_2$— | |
| 45 | 2,6-(CH$_3$)$_2$—C$_6$H$_3$—O— | —CH$_2$—CH$_2$— | |
| 46 | 2,5,6-(CH$_3$)$_3$—C$_6$H$_2$—O— | —CH$_2$—CH$_2$— | |
| 47 | 2,4,5-(CH$_3$)$_3$—C$_6$H$_2$—O— | —CH$_2$—CH$_2$— | |
| 48 | 2-i-C$_3$H$_7$-5-CH$_3$—C$_6$H$_3$—O— | —CH$_2$—CH$_2$— | |
| 49 | 3,5-(C$_2$H$_5$)$_2$—C$_6$H$_3$—O— | —CH$_2$—CH$_2$— | |
| 50 | 2,4,6-(sec-butyl)$_3$-C$_6$H$_2$—O— | —CH$_2$—CH$_2$— | |
| 51 | 3,5-(OCH$_3$)$_2$—C$_6$H$_3$—O— | —CH$_2$—CH$_2$— | |
| 52 | 2-OCH$_3$-4-CH$_3$—C$_6$H$_3$—O— | —CH$_2$—CH$_2$— | |
| 53 | 2,6-(CH$_3$)$_2$-4-SCH$_3$—C$_6$H$_2$—O— | —CH$_2$—CH$_2$— | |
| 54 | 2-Cl-5-OCH$_3$—C$_6$H$_3$—O— | —CH$_2$—CH$_2$— | |
| 55 | 2-CH$_3$-4-SCH$_3$—C$_6$H$_3$—O— | —CH$_2$—CH$_2$— | |
| 56 | 2,6-(OCH$_3$)$_2$—C$_6$H$_3$—O— | —CH$_2$—CH$_2$— | |
| 57 | 2-Cl-4-C$_6$H$_5$—C$_6$H$_3$—O— | —CH$_2$—CH$_2$— | |
| 58 | 2-Cl-4-CH$_3$—C$_6$H$_3$—O— | —CH$_2$—CH$_2$— | |
| 59 | 2-CH$_3$-6-i-C$_3$H$_7$—C$_6$H$_3$—O— | —CH$_2$—CH$_2$— | |
| 60 | 3-t-C$_4$H$_9$-4-OCH$_3$—C$_6$H$_3$—O— | —CH$_2$—CH$_2$— | |
| 61 | 2,4-(CH$_3$)$_2$-1-naphthol | —CH$_2$—CH$_2$— | |
| 62 | C$_6$H$_5$—S— | —CH$_2$—CH$_2$— | |
| 63 | 4-Cl—C$_6$H$_4$—S— | —CH$_2$—CH$_2$— | |
| 64 | 2,4,6-Cl$_3$—C$_6$H$_2$—O— | —CH$_2$—CH(CH$_3$)— | |
| 65 | C$_6$H$_5$—O— | —CH$_2$—CH(CH$_3$)— | |
| 66 | C$_6$H$_5$—O— | —(CH$_2$)$_3$— | oil (E) |
| 67 | 2-F—C$_6$H$_4$—O— | —(CH$_2$)$_3$— | |
| 68 | 3-F—C$_6$H$_4$—O— | —(CH$_2$)$_3$— | |
| 69 | 4-F—C$_6$H$_4$—O— | —(CH$_2$)$_3$— | |
| 70 | 2-Cl—C$_6$H$_4$—O— | —(CH$_2$)$_3$— | |
| 71 | 3-Cl—C$_6$H$_4$—O— | —(CH$_2$)$_3$— | |
| 72 | 4-Cl—C$_6$H$_4$—O— | —(CH$_2$)$_3$— | |
| 73 | 2-CH$_3$—C$_6$H$_4$—O— | —(CH$_2$)$_3$— | |
| 74 | 3-CH$_3$—C$_6$H$_4$—O— | —(CH$_2$)$_3$— | |
| 75 | 4-CH$_3$—C$_6$H$_4$—O— | —(CH$_2$)$_3$— | |
| 76 | 2-OCH$_3$—C$_6$H$_4$—O— | —(CH$_2$)$_3$— | |
| 77 | 3-OCH$_3$—C$_6$H$_4$—O— | —(CH$_2$)$_3$— | |
| 78 | 4-OCH$_3$—C$_6$H$_4$—O— | —(CH$_2$)$_3$— | |
| 79 | 4-t-C$_4$H$_9$—C$_6$H$_4$—O— | —(CH$_2$)$_3$— | |
| 80 | 4-OC$_2$H$_5$—C$_6$H$_4$—O— | —(CH$_2$)$_3$— | |
| 81 | 4-CF$_3$—C$_6$H$_4$—O— | —(CH$_2$)$_3$— | |
| 82 | 4-C$_6$H$_5$—C$_6$H$_4$—O— | —(CH$_2$)$_3$— | |
| 83 | 4-(C$_6$H$_5$—CH$_2$—O)—C$_6$H$_4$—O— | —(CH$_2$)$_3$— | |
| 84 | 2,4,6-Cl$_3$—C$_6$H$_2$—O— | —(CH$_2$)$_3$— | |
| 85 | 2,4,6-(CH$_3$)$_3$—C$_6$H$_2$—O— | —(CH$_2$)$_3$— | |
| 86 | 1-naphthol | —(CH$_2$)$_3$— | |
| 87 | 2-naphthol | —(CH$_2$)$_3$— | |
| 88 | 2,4-Cl$_2$—C$_6$H$_3$—O— | —(CH$_2$)$_3$— | |
| 89 | 3,5-Cl$_2$—C$_6$H$_3$—O— | —(CH$_2$)$_3$— | |
| 90 | 3,4-Cl$_2$—C$_6$H$_3$—O— | —(CH$_2$)$_3$— | |
| 91 | 2,6-(CH$_3$)$_2$—C$_6$H$_3$—O— | —(CH$_2$)$_3$— | |
| 92 | 2,4-(CH$_3$)$_2$—C$_6$H$_3$—O— | —(CH$_2$)$_3$— | |
| 93 | 3-CF$_3$—C$_6$H$_4$—O— | —(CH$_2$)$_3$— | |
| 94 | 2-Cl-4-CH$_3$—C$_6$H$_3$—O— | —(CH$_2$)$_3$— | |
| 95 | C$_6$H$_5$—S— | —(CH$_2$)$_3$— | |
| 96 | C$_6$H$_5$—CH$_2$—O— | —(CH$_2$)$_3$— | |
| 97 | C$_6$H$_5$—O— | —(CH$_2$)$_4$— | 88° C. (E) |
| 98 | 2-F—C$_6$H$_4$—O— | —(CH$_2$)$_4$— | |
| 99 | 3-F—C$_6$H$_4$—O— | —(CH$_2$)$_4$— | |
| 100 | 4-F—C$_6$H$_4$—O— | —(CH$_2$)$_4$— | |
| 101 | 2-CH$_3$—C$_6$H$_4$—O— | —(CH$_2$)$_4$— | |
| 102 | 3-CH$_3$—C$_6$H$_4$—O— | —(CH$_2$)$_4$— | |
| 103 | 4-CH$_3$—C$_6$H$_4$—O— | —(CH$_2$)$_4$— | |
| 104 | 2-OCH$_3$—C$_6$H$_4$—O— | —(CH$_2$)$_4$— | |

TABLE 1-continued

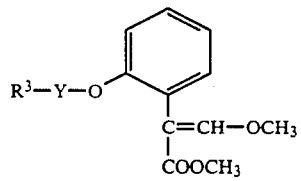

Compounds of the formula I
($R^1$ = $OCH_3$, $R^2$ = $CH_3$, X = CH)
The configuration statement relates to the β-methoxyacrylate group

| No. | $R^3$ | Y | mp. (isomer) |
|---|---|---|---|
| 105 | 3-$OCH_3$—$C_6H_4$—O— | —$(CH_2)_4$— | |
| 106 | 4-$OCH_3$—$C_6H_4$—O— | —$(CH_2)_4$— | |
| 107 | 4-t-$C_4H_9$—$C_6H_4$—O— | —$(CH_2)_4$— | |
| 108 | 4-$OC_2H_5$—$C_6H_4$—O— | —$(CH_2)_4$— | |
| 109 | 4-$CF_3$—$C_6H_4$—O— | —$(CH_2)_4$— | |
| 110 | 4-$C_6H_5$—$C_6H_4$—O— | —$(CH_2)_4$— | |
| 111 | 4-($C_6H_5$—$CH_2$—O)—$C_6H_4$— | —$(CH_2)_4$— | |
| 112 | 2,4,6-$Cl_3$—$C_6H_2$—O— | —$(CH_2)_4$— | |
| 113 | 2,4,6-($CH_3$)—$C_6H_2$—O— | —$(CH_2)_4$— | |
| 114 | 1-naphthol | —$(CH_2)_4$— | |
| 115 | 2-naphthol | —$(CH_2)_4$— | |
| 116 | 3-$CF_3$—$C_6H_4$—O— | —$(CH_2)_4$— | |
| 117 | 3-iso-$C_3H_7$—$C_6H_4$—O— | —$(CH_2)_4$— | |
| 118 | 4-iso-$C_3H_7$—$C_6H_4$—O— | —$(CH_2)_4$— | |
| 119 | 3-t-$C_4H_9$—$C_6H_4$—O— | —$(CH_2)_4$— | |
| 120 | 4-t-butoxy-$C_6H_4$—O— | —$(CH_2)_4$— | |
| 121 | 3-$C_6H_5$—$C_6H_4$—O— | —$(CH_2)_4$— | |
| 122 | 2,4-$Cl_2$—$C_6H_3$—O— | —$(CH_2)_4$— | |
| 123 | 3,4-$Cl_2$—$C_6H_3$—O— | —$(CH_2)_4$— | |
| 124 | 3,5-$Cl_2$—$C_6H_3$—O— | —$(CH_2)_4$— | |
| 125 | 2,6-$Cl_2$—$C_6H_3$—O— | —$(CH_2)_4$— | |
| 126 | 2-Cl-4-$CH_3$—$C_6H_3$—O— | —$(CH_2)_4$— | |
| 127 | 2,6-($CH_3$)$_2$—$C_6H_3$—O— | —$(CH_2)_4$— | |
| 128 | 2,5-($CH_3$)$_2$—$C_6H_3$—O— | —$(CH_2)_4$— | |
| 129 | 4-CN—$C_6H_4$—O— | —$(CH_2)_4$— | |
| 130 | $C_6H_5$—S— | —$(CH_2)_4$— | |
| 131 | $C_6H_5$—$CH_2$—O— | —$(CH_2)_4$— | |
| 132 | $C_6H_5$—O— | —$CH_2$—CH=CH—$CH_2$— | |
| 133 | 2-F—$C_6H_4$—O— | —$CH_2$—CH=CH—$CH_2$— | |
| 134 | 3-F—$C_6H_4$—O— | —$CH_2$—CH=CH—$CH_2$— | |
| 135 | 4-F—$C_6H_4$—O— | —$CH_2$—CH=CH—$CH_2$— | |
| 136 | 2-Cl—$C_6H_4$—O— | —$CH_2$—CH=CH—$CH_2$— | |
| 137 | 3-Cl—$C_6H_4$—O— | —$CH_2$—CH=CH—$CH_2$— | |
| 138 | 4-Cl—$C_6H_4$—O— | —$CH_2$—CH=CH—$CH_2$— | |
| 139 | $C_6H_5$—O— | —$(CH_2)_5$— | |
| 140 | 2-Cl—$C_6H_4$—O— | —$(CH_2)_5$— | oil (E) |
| 141 | 3-Cl—$C_6H_4$—O— | —$(CH_2)_5$— | |
| 142 | 4-Cl—$C_6H_4$—O— | —$(CH_2)_5$— | |
| 143 | 2-F—$C_6H_4$—O— | —$(CH_2)_5$— | |
| 144 | 3-F—$C_6H_4$—O— | —$(CH_2)_5$— | |
| 145 | 4-F—$C_6H_4$—O— | —$(CH_2)_5$— | |
| 146 | 2-$CH_3$—$C_6H_4$—O— | —$(CH_2)_5$— | |
| 147 | 3-$CH_3$—$C_6H_4$—O— | —$(CH_2)_5$— | |
| 148 | 4-$CH_3$—$C_6H_4$—O— | —$(CH_2)_5$— | |
| 149 | 2-$OCH_3$—$C_6H_4$—O— | —$(CH_2)_5$— | |
| 150 | 3-$OCH_3$—$C_6H_4$—O— | —$(CH_2)_5$— | |
| 151 | 4-$OCH_3$—$C_6H_4$—O— | —$(CH_2)_5$— | |
| 152 | 4-t-$C_4H_9$—$C_6H_4$—O— | —$(CH_2)_5$— | |
| 153 | 4-$OC_2H_5$—$C_6H_4$—O— | —$(CH_2)_5$— | |
| 154 | 4-$CF_3$—$C_6H_4$—O— | —$(CH_2)_5$— | |
| 155 | 4-$C_6H_5$—$C_6H_4$—O— | —$(CH_2)_5$— | |
| 156 | 4-($C_6H_5$—$CH_2$—O)—$C_6H_4$—O— | —$(CH_2)_5$— | |
| 157 | 2,4,6-$Cl_3$—$C_6H_2$—O— | —$(CH_2)_5$— | |
| 158 | 2,4,6-($CH_3$)$_3$—$C_6H_2$—O— | —$(CH_2)_5$— | |
| 159 | 1-naphthol | —$(CH_2)_5$— | |
| 160 | 2-naphthol | —$(CH_2)_5$— | |
| 161 | $C_6H_5$—$CH_2$—O— | —$(CH_2)_5$— | |
| 162 | $C_6H_5$—O— | —$(CH_2)_6$— | 88° C. (E) |
| 163 | 2-Cl—$C_6H_4$—O— | —$(CH_2)_6$— | oil (E) |
| 164 | 2-Cl—$C_6H_4$—O— | —$(CH_2)_6$— | oil (E/Z = 3/1) |
| 165 | 3-Cl—$C_6H_4$—O— | —$(CH_2)_6$— | |
| 166 | 4-Cl—$C_6H_4$—O— | —$(CH_2)_6$— | 59° C. (E) |
| 167 | 2-F—$C_6H_4$—O— | —$(CH_2)_6$— | |
| 168 | 3-F—$C_6H_4$—O— | —$(CH_2)_6$— | |
| 169 | 4-F—$C_6H_4$—O— | —$(CH_2)_6$— | |
| 170 | 2-$CH_3$—$C_6H_4$—O— | —$(CH_2)_6$— | |
| 171 | 3-$CH_3$—$C_6H_4$—O— | —$(CH_2)_6$— | |
| 172 | 4-$CH_3$—$C_6H_4$—O— | —$(CH_2)_6$— | |

TABLE 1-continued

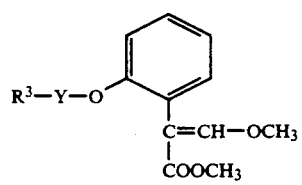

Compounds of the formula I
($R^1$ = $OCH_3$, $R^2$ = $CH_3$, X = CH)
The configuration statement relates to the β-methoxyacrylate group

| No. | $R^3$ | Y | mp. (isomer) |
|---|---|---|---|
| 173 | 2-$OCH_3$—$C_6H_4$—O— | —$(CH_2)_6$— | |
| 174 | 3-$OCH_3$—$C_6H_4$—O— | —$(CH_2)_6$— | |
| 175 | 4-$OCH_3$—$C_6H_4$—O— | —$(CH_2)_6$— | |
| 176 | 4-t-$C_4H_9$—$C_6H_4$—O— | —$(CH_2)_6$— | |
| 177 | 4-$OC_2H_5$—$C_6H_4$—O— | —$(CH_2)_6$— | |
| 178 | 4-$CF_3$—$C_6H_4$—O— | —$(CH_2)_6$— | |
| 179 | 4-$C_6H_5$—$C_6H_4$—O— | —$(CH_2)_6$— | |
| 180 | 4-($C_6H_5$—$CH_2$—O)—$C_6H_4$—O— | —$(CH_2)_6$— | |
| 181 | 2,4,6-$Cl_3$—$C_6H_2$—O— | —$(CH_2)_6$— | |
| 182 | 2,4,6-$(CH_3)_3$—$C_6H_2$—O— | —$(CH_2)_6$— | |
| 183 | 1-naphthol | —$(CH_2)_6$— | |
| 184 | 2-naphthol | —$(CH_2)_6$— | |
| 185 | $C_6H_5$—$CH_2$—O— | —$(CH_2)_6$— | |
| 186 | $C_6H_5$—O— | —$(CH_2)_7$— | |
| 187 | 2-Cl—$C_6H_4$—O— | —$(CH_2)_7$— | |
| 188 | 3-Cl—$C_6H_4$—O— | —$(CH_2)_7$— | |
| 189 | 4-Cl—$C_6H_4$—O— | —$(CH_2)_7$— | |
| 190 | 2-F—$C_6H_4$—O— | —$(CH_2)_7$— | |
| 191 | 3-F—$C_6H_4$—O— | —$(CH_2)_7$— | |
| 192 | 4-F—$C_6H_4$—O— | —$(CH_2)_7$— | |
| 193 | 2-$CH_3$—$C_6H_4$—O— | —$(CH_2)_7$— | |
| 194 | 3-$CH_3$—$C_6H_4$—O— | —$(CH_2)_7$— | |
| 195 | 4-$CH_3$—$C_6H_4$—O— | —$(CH_2)_7$— | oil (E) |
| 196 | 2-$OCH_3$—$C_6H_4$—O— | —$(CH_2)_7$— | |
| 197 | 3-$OCH_3$—$C_6H_4$—O— | —$(CH_2)_7$— | |
| 198 | 4-$OCH_3$—$C_6H_4$—O— | —$(CH_2)_7$— | oil (E) |
| 199 | 4-t-$C_4H_9$—$C_6H_4$—O— | —$(CH_2)_7$— | |
| 200 | 4-$OC_2H_5$—$C_6H_4$—O— | —$(CH_2)_7$— | |
| 201 | 4-$CF_3$—$C_6H_4$—O— | —$(CH_2)_7$— | |
| 202 | 4-$C_6H_5$—$C_6H_4$—O— | —$(CH_2)_7$— | |
| 203 | 2,4,6-$(Cl_3)_3$—$C_6H_2$—O— | —$(CH_2)_7$— | |
| 204 | 2,4,6-$(CH_3$—$C_6H_2$—O— | —$(CH_2)_7$— | |
| 205 | 1-naphthol | —$(CH_2)_7$— | |
| 206 | 2-naphthol | —$(CH_2)_7$— | |
| 207 | 4-($C_6H_5$—$CH_2$—O)—$C_6H_4$—O— | —$(CH_2)_7$— | |
| 208 | $C_6H_5$—$CH_2$—O— | —$(CH_2)_7$— | |
| 209 | $C_6H_5$—O— | —$(CH_2)_8$— | oil (E) |
| 210 | 2-Cl—$C_6H_4$—O— | —$(CH_2)_8$— | |
| 211 | 3-Cl—$C_6H_4$—O— | —$(CH_2)_8$— | |
| 212 | 4-Cl—$C_6H_4$—O— | —$(CH_2)_8$— | |
| 213 | 2-F—$C_6H_4$—O— | —$(CH_2)_8$— | |
| 214 | 3-F—$C_6H_4$—O— | —$(CH_2)_8$— | |
| 215 | 4-F—$C_6H_4$—O— | —$(CH_2)_8$— | |
| 216 | 2-$CH_3$—$C_6H_4$—O— | —$(CH_2)_8$— | |
| 217 | 3-$CH_3$—$C_6H_4$—O— | —$(CH_2)_8$— | |
| 218 | 4-$CH_3$—$C_6H_4$—O— | —$(CH_2)_8$— | |
| 219 | 2-$OCH_3$—$C_6H_4$—O— | —$(CH_2)_8$— | |
| 220 | 3-$OCH_3$—$C_6H_4$—O— | —$(CH_2)_8$— | |
| 221 | 4-$OCH_3$—$C_6H_4$—O— | —$(CH_2)_8$— | |
| 222 | 4-t-$C_4H_9$—$C_6H_4$—O— | —$(CH_2)_8$— | |
| 223 | 4-$OC_2H_5$—$C_6H_4$—O— | —$(CH_2)_8$— | |
| 224 | 4-$CF_3$—$C_6H_4$—O— | —$(CH_2)_8$— | |
| 225 | 4-$C_6H_5$—$C_6H_4$—O— | —$(CH_2)_8$— | |
| 226 | 4-($C_6H_5$—$CH_2$—O)—$C_6H_4$—O— | —$(CH_2)_8$— | |
| 227 | 2,4,6-$Cl_3$—$C_6H_2$—O— | —$(CH_2)_8$— | |
| 228 | 2,4,6-$(CH_3)_3$—$C_6H_2$—O— | —$(CH_2)_8$— | |
| 229 | 1-naphthol | —$(CH_2)_8$— | |
| 230 | 2-naphthol | —$(CH_2)_8$— | |
| 231 | $C_6H_5$—$CH_2$—O— | —$(CH_2)_8$— | |
| 232 | $C_6H_5$—O— | —$(CH_2)_9$— | oil (E) |
| 233 | $C_6H_5$—O— | —$(CH_2)_{10}$— | 56° C. (E) |
| 234 | 2-Cl—$C_6H_4$—O— | —$(CH_2)_{10}$— | |
| 235 | 3-Cl—$C_6H_4$—O— | —$(CH_2)_{10}$— | |
| 236 | 4-Cl—$C_6H_4$—O— | —$(CH_2)_{10}$— | |
| 237 | 2-F—$C_6H_4$—O— | —$(CH_2)_{10}$— | |
| 238 | 3-F—$C_6H_4$—O— | —$(CH_2)_{10}$— | |
| 239 | 4-F—$C_6H_4$—O— | —$(CH_2)_{10}$— | |
| 240 | 2-$CH_3$—$C_6H_4$—O— | —$(CH_2)_{10}$— | |

TABLE 1-continued

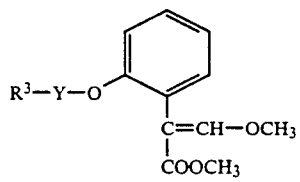

Compounds of the formula I
($R^1 = OCH_3$, $R^2 = CH_3$, $X = CH$)
The configuration statement relates to the β-methoxyacrylate group

| No. | $R^3$ | Y | mp. (isomer) |
|---|---|---|---|
| 241 | 3-$CH_3$—$C_6H_4$—O— | —$(CH_2)_{10}$— | |
| 242 | 4-$CH_3$—$C_6H_4$—O— | —$(CH_2)_{10}$— | |
| 243 | 2-$OCH_3$—$C_6H_4$—O— | —$(CH_2)_{10}$— | |
| 244 | 3-$OCH_3$—$C_6H_4$—O— | —$(CH_2)_{10}$— | |
| 245 | 4-$OCH_3$—$C_6H_4$—O— | —$(CH_2)_{10}$— | |
| 246 | 4-t-$C_4H_9$—$C_6H_4$—O— | —$(CH_2)_{10}$— | |
| 247 | 4-$OC_2H_5$—$C_6H_4$—O— | —$(CH_2)_{10}$— | |
| 248 | 4-$CF_3$—$C_6H_4$—O— | —$(CH_2)_{10}$— | |
| 249 | 4-$C_6H_5$—$C_6H_4$—O— | —$(CH_2)_{10}$— | |
| 250 | 4-($C_6H_5$—$CH_2$—O)—$C_6H_4$—O— | —$(CH_2)_{10}$— | |
| 251 | 2,4,6-$Cl_3$—$C_6H_2$—O— | —$(CH_2)_{10}$— | |
| 252 | 2,4,6-$(CH_3)_3$—$C_6H_2$—O— | —$(CH_2)_{10}$— | |
| 253 | 1-naphthol | —$(CH_2)_{10}$— | |
| 254 | 2-naphthol | —$(CH_2)_{10}$— | |
| 255 | $C_6H_5$—$CH_2$—O— | —$(CH_2)_{10}$— | |
| 280 | 2,4-$Cl_2$—$C_6H_3$—O— | —$(CH_2)_6$— | oil (E) |
| 281 | 2,6-$Cl_2$—$C_6H_3$—O— | —$(CH_2)_6$— | oil (E) |
| 282 | 4-Cl—$C_6H_4$—O— | —$(CH_2)_{12}$— | 61° C. (E) |

TABLE 2

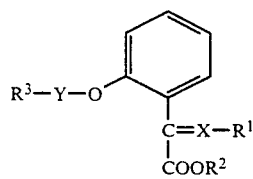

Compounds of the formula I

| No. | $R^1$ | $R^2$ | $R^3$ | X | Y | mp. (isomer) |
|---|---|---|---|---|---|---|
| 256 | $CH_3$ | $CH_3$ | $C_6H_5$—O | CH | $(CH_2)_4$ | |
| 257 | $CH_3$ | $CH_3$ | 2-Cl—$C_6H_4$—O— | CH | $(CH_2)_5$ | |
| 258 | $CH_3$ | $CH_3$ | 2-Cl—$C_6H_4$—O— | CH | $(CH_2)_6$ | |
| 259 | $C_2H_5$ | $CH_3$ | $C_6H_5$—O— | CH | $(CH_2)_4$ | |
| 260 | $C_2H_5$ | $CH_3$ | 2-Cl—$C_6H_4$—O— | CH | $(CH_2)_5$ | |
| 261 | $C_2H_5$ | $CH_3$ | 2-Cl—$C_6H_4$—O— | CH | $(CH_2)_6$ | |
| 262 | $SCH_3$ | $CH_3$ | $C_6H_5$—O— | CH | $(CH_2)_4$ | |
| 263 | $SCH_3$ | $CH_3$ | 2-Cl—$C_6H_5$—O— | CH | $(CH_2)_5$ | |
| 264 | $SCH_3$ | $CH_3$ | 2-Cl—$C_6H_5$—O— | CH | $(CH_2)_6$ | |
| 265 | $NHCH_3$ | $CH_3$ | $C_6H_5$—O— | CH | $(CH_2)_4$ | |
| 266 | $NHCH_3$ | $CH_3$ | 2-Cl—$C_6H_4$—O— | CH | $(CH_2)_5$ | |
| 267 | $NHCH_3$ | $CH_3$ | 2-Cl—$C_6H_4$—O— | CH | $(CH_2)_6$ | |
| 268 | $N(CH_3)_2$ | $CH_3$ | $C_6H_5$—O— | CH | $(CH_2)_4$ | |
| 269 | $N(CH_3)_2$ | $CH_3$ | 2-Cl—$C_6H_4$—O— | CH | $(CH_2)_5$ | |
| 270 | $N(CH_3)_2$ | $CH_3$ | 2-Cl—$C_6H_4$—O— | CH | $(CH_2)_6$ | |
| 271 | $OCH_3$ | $CH_3$ | $C_6H_5$—O— | N | $(CH_2)_4$ | |
| 272 | $OCH_3$ | $CH_3$ | 2-Cl—$C_6H_4$—O— | N | $(CH_2)_5$ | |
| 273 | $OCH_3$ | $CH_3$ | 2-Cl—$C_6H_4$—O— | N | $(CH_2)_6$ | |
| 274 | $NHCH_3$ | $CH_3$ | $C_6H_5$—O— | N | $(CH_2)_4$ | |
| 275 | $NHCH_3$ | $CH_3$ | 2-Cl—$C_6H_4$—O— | N | $(CH_2)_5$ | |
| 276 | $NHCH_3$ | $CH_3$ | 2-Cl—$C_6H_4$—O— | N | $(CH_2)_6$ | |
| 277 | $N(CH_3)_2$ | $CH_3$ | $C_6H_5$—O— | N | $(CH_2)_4$ | |
| 278 | $N(CH_3)_2$ | $CH_3$ | 2-Cl—$C_6H_4$—O— | N | $(CH_2)_5$ | |
| 279 | $N(CH_3)_2$ | $CH_3$ | 2-Cl—$C_6H_4$—O— | N | $(CH_2)_6$ | |
| 283 | $OCH_3$ | $CH_3$ | $C_6H_5$—O— | N | $(CH_2)_2$ | 98-101° C. (E/Z = 2/1) |
| 284 | $OCH_3$ | $CH_3$ | 2-Cl—$C_6H_4$—O— | N | $(CH_2)_2$ | |
| 285 | $OCH_3$ | $CH_3$ | 3-Cl—$C_6H_4$—O— | N | $(CH_2)_2$ | |
| 286 | $OCH_3$ | $CH_3$ | 2,6-$Cl_2$—$C_6H_3$—O— | N | $(CH_2)_4$ | |
| 287 | $OCH_3$ | $CH_3$ | 4-$OCH_3$—$C_6H_4$—O— | N | $(CH_2)_4$ | |
| 288 | $OCH_3$ | $CH_3$ | 2-F—$C_6H_4$—O— | N | $(CH_2)_5$ | |
| 289 | $OCH_3$ | $CH_3$ | 3,5-$Cl_2$—$C_6H_3$—O— | N | $(CH_2)_{10}$ | |

TABLE 3

NMR data of selected compounds from Tables 1 and 2. The chemical shift (δ) is given in ppm relative to tetramethylsilane. The solvent employed is CDCl$_3$.

Compound no. 66; 2.17 (q,2H); 3.60 (s,3H); 3.71 (s,3H); 4.11 (m,4H); 7.08 (m,9H); 7.47 (s,1H).

Compound no. 97; 2.88 (m,4H); 3.68 (s,3H); 3.77 (s,3H); 4.00 (m,4H); 7.08 (m,9H); 7.48 (s,1H).

Compound no. 140; 1.63 (m,2H); 2.85 (m,4H); 3.66 (s,3H); 3.80 (s,3H); 3.98 (t,2H); 4.05 (t,2H); 7.12 (m,8H); 7.50 (s,1H).

Compound no. 163; 1.50 (m,4H); 1.75 (m,4H); 3.67 (s,3H); 3.78 (s,3H); 3.94 (t,2H); 4.03 (t,2H); 7.12 (m,8H); 7.49 (s,1H).

Compound no. 195; 1.41 (m,6H); 1.75 (m,4H); 2.28 (s,3H); 3.68 (s,3H); 3.80 (s,3H); 3.90 (t,2H); 3.93 (t,2H); 7.00 (m,8H); 7.48 (s,1H).

Compound no. 209; 1.36 (m,8H); 1.72 (m,4H); 3.65 (s,3H); 3.75 (s,3H); 3.89 (t,2H); 3.92 (t,2H); 6.79-7.28 (m,9H); 7.45 (s,1H).

Compound no. 232; 1.33 (m,10H); 1.73 (m,4H); 3.68 (s,3H); 3.80 (s,3H); 3.90 (t,2H); 3.94 (t,2H); 6.84-7.70 (m,9H); 7.48 (s,1H).

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,

*Erysiphe cichoracearum* and *Sphaerotheca fuliginea* in cucurbits,

*Podosphaera leucotricha* in apples,

*Uncinula necator* in vines,

Puccinia species in cereals,

*Rhizoctonia solani* in cotton,

Ustilago species in cereals and sugar cane,

*Venturia inaequalis* (scab) in apples,

Helminthosporium species in cereals,

*Septoria nodorum* in wheat,

*Botrytis cinerea* (gray mold) in strawberries and grapes,

*Cercospora arachidicola* in groundnuts,

*Pseudocercosporella herpotrichoides* in wheat and barley,

*Pyricularia oryzae* in rice,

*Phytophthora infestans* in potatoes and tomatoes,

Fusarium and Verticillium species in various plants,

*Plasmopara viticola* in grapes,

Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering. Examples of formulations are given below.

I. 90 parts by weight of compound no. 66 is mixed with 10 parts by weight of N-methyl-α-pyrrolidone. A mixture is obtained which is suitable for application in the form of very fine drops.

II. 20 parts by weight of compound no. 97 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 140 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 164 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 163 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 66 is intimately mixed with 97 parts by weight of particulate kaolin. A dust is obtained containing 3% by weight of the active ingredient.

VII. 30 parts by weight of compound no. 97 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 140 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 163 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
Sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, N-tridecyl-2,6-dimethylmorpholine (A) disclosed in DE-1,164,152 was used.

USE EXAMPLE 1

Action on *Pyrenophora teres*

Barley seedlings of the "Igri" variety were sprayed to runoff at the two-leaf stage with aqueous suspensions containing (dry basis) 80 wt % of active ingredient and 20% of emulsifier. After 24 hours, the plants were inoculated with a spore suspension of the fungus *Pyrenophora teres* and placed for 48 hours in a high-humidity climatic cabinet at 18° C. The plants were then cultivated in the greenhouse at from 20° to 22° C. and a relative humidity of 70% for a further 5 days. The extent of the spread of the symptoms was then assessed.

The results show that active ingredients 97, 140 and 164, applied as 0.05% spray liquors, have a better fungicidal action (97%) than prior art active ingredient A (70%).

USE EXAMPLE 2

Action on *Phytophthora infestans* in tomatoes

The leaves of potted tomatoes of the "Grosse Fleischtomate" variety were sprayed with aqueous liquors containing (dry basis) 80% of active ingredient and 20% of emulsifier. After 24 hours, the leaves were infected with a zoospore suspension of the fungus *Phytophthora infestans*. The plants were placed in a water vapor-saturated cabinet kept at from 16 to 18° C. After 6 days, the disease had spread to such a considerable extent on the untreated but infected plants that fungicidal effectiveness could be assessed.

The results show that active ingredients 66, 140, 163 and 164 have, when applied as 0.025% spray liquors, a better fungicidal action (95%) than prior art active ingredient A (55%).

USE EXAMPLE 3

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vaporsaturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 66, 97, 140, 163 and 164 have, when applied as 0.05% spray liquors, a better fungicidal action (97%) than prior art active ingredient A (35%).

We claim:

1. Ortho-substituted phenol ethers of the general formula I

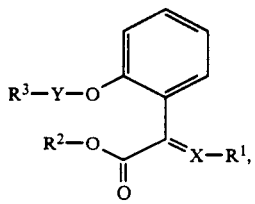

where
R$^1$ is C$_1$-C$_4$-alkyl, C$_1$-C$_4$-alkoxy, C$_1$-C$_4$-alkylthio or amino which is unsubstituted or mono- or disubstituted by C$_1$-C$_4$-alkyl,
R$^2$ is C$_1$-C$_4$-alkyl,
R$^3$ is aryloxy, arylthio or arylalkoxy, the aromatic ring being unsubstituted or substituted by one or more of the following radicals: halogen, C$_1$-C$_6$-alkyl, C$_1$-C$_6$-alkoxy, C$_1$-C$_4$-alkylthio, C$_1$-C$_2$-haloalkyl, aryl, aryl-C$_1$-C$_2$-alkoxy, C$_1$-C$_4$-alkylcarbonyl, mono- or di-C$_1$-C$_4$-alkyl-substituted amino; cyano, nitro,
X is CH or N, and
Y is saturated or unsaturated C$_2$-C$_{12}$-alkylene.

2. A process for combating fungi, wherein the fungi, or the materials, plants, seed or the soil to be protected against fungus attack are treated with a fungicidally effective amount of an ortho-substituted phenol ether of the general formula I

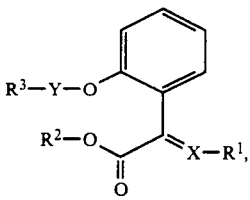

where
R$^1$ is C$_1$-C$_4$-alkyl, C$_1$-C$_4$-alkoxy, C$_1$-C$_4$-alkylthio or amino which is unsubstituted or mono- or disubstituted by C$_1$-C$_4$-alkyl,
R$^2$ is C$_1$-C$_4$-alkyl,
R$^3$ is aryloxy, arylthio or arylalkoxy, the aromatic ring being unsubstituted or substituted by one or more of the following radicals: halogen, C$_1$-C$_6$-alkyl, C$_1$-C$_6$-alkoxy, C$_1$-C$_4$-alkylthio, C$_1$-C$_2$-haloalkyl, aryl, aryl-C$_1$-C$_2$-alkoxy, C$_1$-C$_4$-alkylcarbonyl, mono- or di-C$_1$-C$_4$-alkyl-substituted amino, cyano, nitro,
X is CH or N, and
Y is saturated or unsaturated C$_2$-C$_{12}$-alkylene.

3. A fungicide containing an inert carrier and an ortho-substituted phenol ether of the general formula I

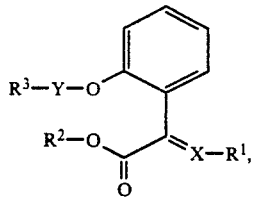

where
- $R^1$ is $C_1$-$C_4$-alkyl, $C_1$-$C_4$-alkoxy, $C_1$-$C_4$-alkylthio or amino which is unsubstituted or mono- or disubstituted by $C_1$-$C_4$-alkyl,
- $R^2$ is $C_1$-$C_4$-alkyl,
- $R^3$ is aryloxy, arylthio or arylalkoxy, the aromatic ring being unsubstituted or substituted by one or more of the following radicals: halogen, $C_1$-$C_6$-alkyl, $C_1$-$C_6$-alkoxy, $C_1$-$C_4$-alkylthio, $C_1$-$C_2$-haloalkyl, aryl, aryl-$C_1$-$C_2$-alkoxy, $C_1$-$C_4$-alkylcarbonyl, mono- or di-$C_1$-$C_4$-alkyl-substituted amino, cyano, nitro,
- X is CH or N, and
- Y is saturated or unsaturated $C_2$-$C_{12}$-alkylene.

4. A compound as set forth in claim 1, where $R^1$ is methoxy, $R^2$ is methyl, $R^3$ is phenoxy, Y is butylene and X is CH.

5. A compound as set forth in claim 1, where $R^1$ is methoxy, $R^2$ is methyl, $R^3$ is 2-chlorophenoxy, Y is pentylene and X is CH.

6. A compound as set forth in claim 1, where $R^1$ is methoxy, $R^2$ is methyl, $R^3$ is 2-chlorophenoxy, Y is hexylene and X is CH.

7. A compound as set forth in claim 1, where $R^1$ is methoxy, $R^2$ is methyl, $R^3$ is phenoxy, Y is propylene and X is CH.

* * * * *

UNITED STATES PATENT AND TRADEMARK OFFICE
CERTIFICATE OF CORRECTION

PATENT NO. : 5,008,438
DATED : April 16, 1991
INVENTOR(S) : Franz Schuetz et al.

It is certified that error appears in the above-identified patent and that said Letters Patent is hereby corrected as shown below:

ON THE TITLE PAGE:   Item [75]
   The second inventor's city is incorrect, should be, --Weinheim--, and the last inventor's name is incorrect, should be, --Gisela Lorenz--.

Signed and Sealed this

Twenty-ninth Day of September, 1992

Attest:

DOUGLAS B. COMER

*Attesting Officer*   *Acting Commissioner of Patents and Trademarks*